(12) United States Patent
Wang et al.

(10) Patent No.: US 10,226,534 B2
(45) Date of Patent: Mar. 12, 2019

(54) SEMI-SOLID DELIVERY SYSTEMS

(71) Applicant: REGENTS OF THE UNIVERSITY OF MINNESOTA, Minneapolis, MN (US)

(72) Inventors: Wenshou Wang, Quincy, MA (US); Chun Wang, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 162 days.

(21) Appl. No.: 15/021,573

(22) PCT Filed: Sep. 12, 2014

(86) PCT No.: PCT/US2014/055506
§ 371 (c)(1),
(2) Date: Mar. 11, 2016

(87) PCT Pub. No.: WO2015/038966
PCT Pub. Date: Mar. 19, 2015

(65) Prior Publication Data
US 2016/0220683 A1 Aug. 4, 2016

Related U.S. Application Data

(60) Provisional application No. 61/960,189, filed on Sep. 12, 2013.

(51) Int. Cl.
| | | |
|---|---|---|
| A61K 47/34 | (2017.01) | |
| A61K 9/06 | (2006.01) | |
| A61K 38/38 | (2006.01) | |
| C08G 65/331 | (2006.01) | |
| A61K 9/51 | (2006.01) | |
| C08G 63/664 | (2006.01) | |
| C08G 81/00 | (2006.01) | |
| C08L 71/02 | (2006.01) | |
| A61K 9/00 | (2006.01) | |

(52) U.S. Cl.
CPC ............... *A61K 47/34* (2013.01); *A61K 9/06* (2013.01); *A61K 9/5153* (2013.01); *A61K 38/385* (2013.01); *C08G 63/664* (2013.01); *C08G 65/3312* (2013.01); *C08G 81/00* (2013.01); *C08L 71/02* (2013.01); *A61K 9/0014* (2013.01); *A61K 9/0019* (2013.01); *A61K 9/0024* (2013.01); *C08G 2650/44* (2013.01)

(58) Field of Classification Search
None
See application file for complete search history.

(56) References Cited

U.S. PATENT DOCUMENTS

| | | |
|---|---|---|
| 4,938,949 A | 7/1990 | Borch et al. |
| 6,613,355 B2 | 9/2003 | Ng et al. |
| 2015/0283244 A1 | 10/2015 | Wang et al. |

FOREIGN PATENT DOCUMENTS

| | | |
|---|---|---|
| CN | 102911368 A | 2/2013 |
| WO | 2003000777 A2 | 1/2003 |

OTHER PUBLICATIONS

Ferruti et al.; Biomacromolecules; 4, pp. 181-188; published on the web Jan. 13, 2003.*
Xiong et al.; Pharmaceutical Research, vol. 25, No. 11, pp. 2555-2566; published Nov. 2008.*
Wang et al.; Journal of Materials Chemistry B, vol. 1, No. 48, pp. 6563-6676; published Dec. 28, 2013.*
Amsden, et al., "Liquid, injectable, hydrophobic and biodegradable polymers as drug delivery vehicles", Macromol Biosci 10 (8), 825-835 (2010).
Heller, et al., "Poly(ortho esters): synthesis, characterization, properties and uses", Adv Drug Deliv Rev 54 (7), 1015-1039 (2002).
Labet, et al., "Synthesis of polycaprolactone: a review", Chem Soc Rev 38 (12), 3484-3504 (2009).
Miao, et al., "Synthesis and properties of a dually cleavable graft copolymer comprising pendant acetal linkages", Polym Chem 5, 1191-1201 (2014).
Patent Cooperation Treaty, International Searching Authority, Search Report and Written Opinion for PCT/US2014/055506, 11 pages, dated Feb. 25, 2015.
Shao, et al., "Acid and reduction dually cleavable amphiphilic comb-like copolymer micelles for controlled drug delivery", Polym Chem 4, 3398-3410 (2013).
Uhrich, et al., "Polymeric systems for controlled drug release", Chem Rev 99 (11), 3181-3198 (1999).
Xiong, et al., "Conjugation of Arginine-Glycine-Aspartic Acid Peptides to Poly(ethylene oxide)-b-poly∊-caprolactone) Micelles for Enhanced Intracellular Drug Delivery to Metastatic Tumor Cells", Biomacromolecules 8, 874-884 (2007).
Zhang, et al., "Synthesis of monomethoxy poly(ethylene glycol) without diol poly(ethylene glycol)", J. Appl. Polym. Sci. 105(6), 3780-3786 (2007).

\* cited by examiner

*Primary Examiner* — Jeffrey T. Palenik
(74) *Attorney, Agent, or Firm* — Viksnins Harris Padys Malen LLP

(57) ABSTRACT

The invention provides semi-solid systems for delivering biologically active materials that include a polymer comprising 1) one or more polycaprolactone (PCL) units and 2) at least one or more polyethylene glycol (PEG) units; wherein at least one of said polycaprolactone units is conjugated to a PEG forming an acetal group.

19 Claims, 13 Drawing Sheets

SEMI-SOLID DELIVERY SYSTEMS

RELATED APPLICATION

This application claims priority to U.S. Provisional Patent Application No. 61/960,189, filed Sep. 12, 2013, the entirety of which is incorporated herein by reference

GOVERNMENT SUPPORT

This invention was made with government support under CA129189 awarded by the National Institutes of Health. The government has certain rights in the invention.

BACKGROUND OF THE INVENTION

Because of their excellent biocompatibility and adjustable degradation rate, biodegradable and biocompatible polymers have been extensively studied as drug controlled release carriers. Besides selecting the optimal polymer for specific drug delivery purpose, how to incorporate drugs efficiently into polymers is another important issue. Polymers have been prepared into different physical forms, such as micelles, nanoparticles, microspheres, films, gels, to facilitate the encapsulation and controlled release of drugs (see Uhrich, K. E., et al., Chem. Rev. 1999, 99, 3181-3198). In spite of all the advances made, there is much to be further improved. First, most micelles, microspheres or particles often have low drug loading efficiency, as low as a few percent in some cases. Second, many formulation technologies need the assistance of organic solvents to dissolve drugs during dosage preparation and processing. However, the use of organic solvents might be detrimental to delicate drugs such as proteins or peptides, and the residual solvent could be a safety concern for human use. The emergence of injectable biodegradable polymers holds promise in solving these problems (see Amsden, B. Macrom. Biosci. 2010, 10, 825-835; and Heller, J, et al., Adv. Drug Deliv. Rev. 2002, 54, 1015-1039). Drugs could be mixed with or dissolved in viscous semi-solid polymers directly at room temperature with loading efficiency of 100%, and the facile incorporation is especially beneficial for those thermally sensitive or solvent-sensitive drugs such as proteins and peptides. The injectability of semi-solid polymers and administration via minimally invasive means is another advantage.

Currently there remains is a large unmet need for better delivery systems to achieve sustained release of drugs and other biologically active agents at prescribed durations.

SUMMARY OF THE INVENTION

A new polymer material has been identified that is a semi-solid at room and physiological temperatures allowing easy formulation of drugs (e.g. by simple mixing) and delivery by minimally invasive injection or topical application (to the skin). The material is capable of loading and releasing a wide range of drugs either hydrophobic or hydrophilic, including small molecule drugs, and macromolecular drugs such as proteins, peptides, polysaccharides, nucleic acids. For example, the polymers can be used to deliver tumor antigens and immunostimulatory adjuvants. Additionally, the polymer chemistry utilized for the preparation of the semi-solid polymers allows for easy tuning of drug release rate to suit different application requirement. The materials have the additional advantages of being synthesized easily from biocompatible building blocks, so that the degradation products are biocompatible. The materials also offer the advantage of being synthesized using commonly available molecules, so that their preparation is cost-effective.

Accordingly, in an aspect of the invention there is provided a polymer comprising 1) one or more polycaprolactone (PCL) units and 2) at least one or more polyethylene glycol units (PEG); wherein at least one of said polycaprolactone units is conjugated to a PEG forming an acetal group.

The invention also provides a pharmaceutical composition comprising a polymer of the invention and a biologically active agent.

The polymers of the invention can be used as a controlled release system for a very broad range of cargos including small molecular drugs, large molecular drugs such as proteins (including antibodies), peptides, polysaccharides, nucleic acids, or multiple cargos of these kinds combined in a single system. The material is a semi-solid so it is most suited for parenteral delivery of drugs through injection or topical application to the skin. Applications include drug delivery in disease treatments that require parenteral delivery, such as cancer therapy, anti-inflammatory anti-infectious therapies, neurological drug therapy including pain relief, vaccine formulation and adjuvant delivery, and drug therapies to treat skin disorders and metabolic diseases such as diabetes.

The invention also provides processes and intermediates disclosed herein that are useful for preparing the polymers of the invention.

DETAILED DESCRIPTION

Figure 1:
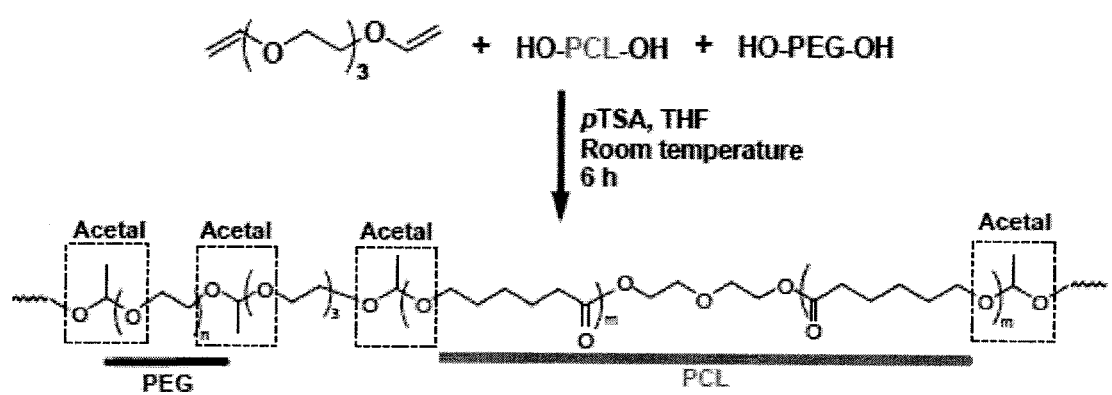
FIG. 1. Illustration of the synthesis of semi-solid polymers PCL-PEG-AT. The molar ratio between the sum of PCL diol and PEG diol versus divinyl ether was 1:1.
Figure 2:
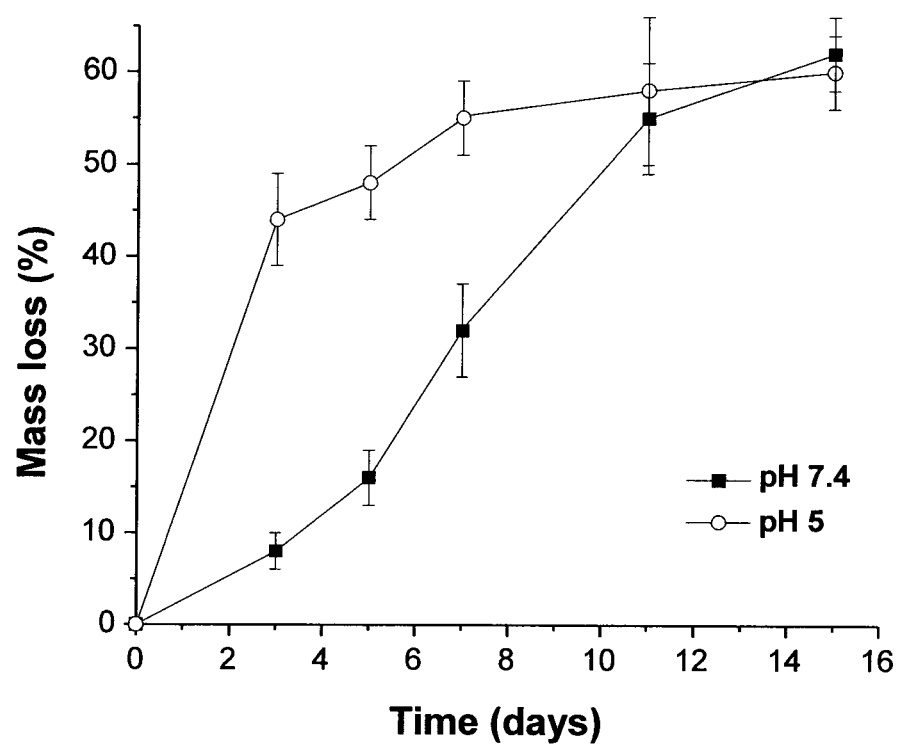
FIG. 2. Mass loss of PCL-PEG-AT in aqueous buffers of pH 7.4 and pH 5.0. Acidic pH accelerated polymer erosion is apparent.
Figure 3:
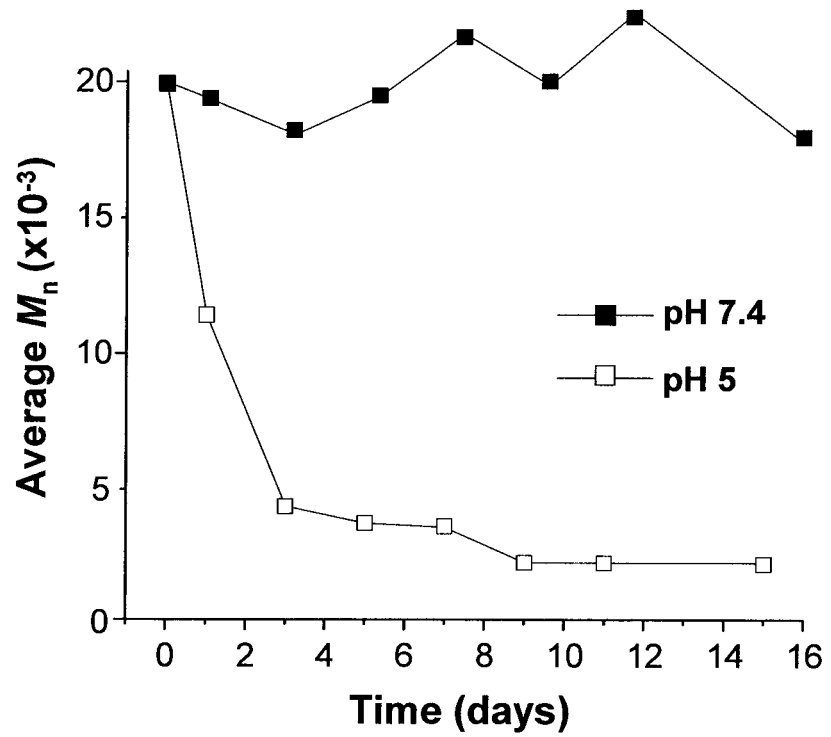
FIG. 3. Hydrolytic degradation, measured by changes in average molecular weight, of the PCL-PEG-AT polymer at different pH. At pH 5 polymer degradation was essentially complete in the first 3 days, whereas the polymer was stable at pH 7.4.
Figure 4:
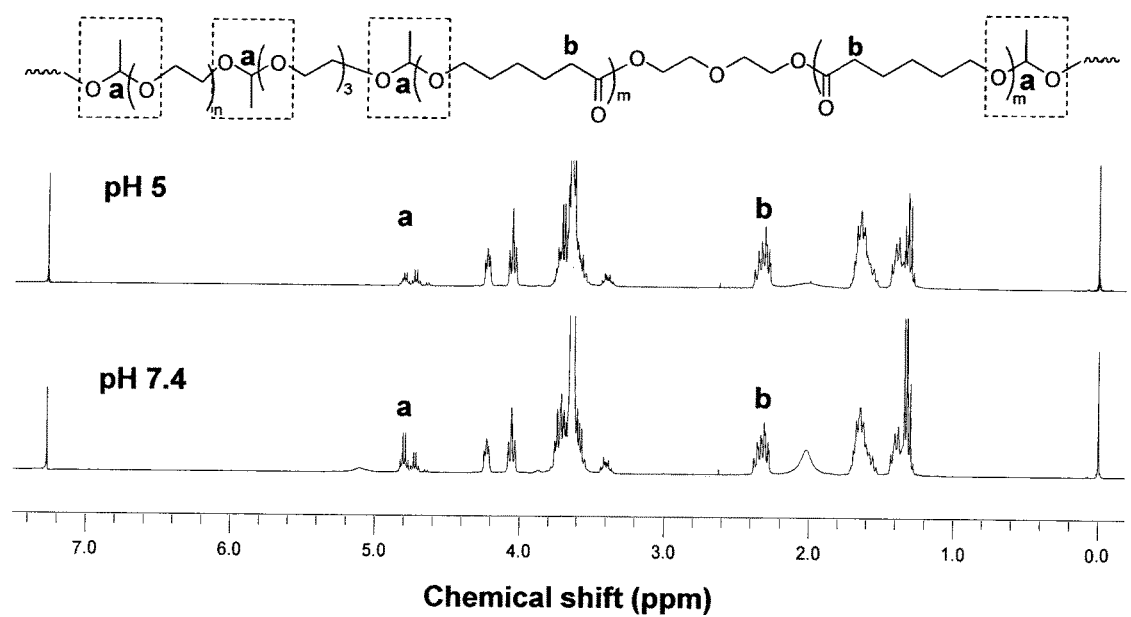
FIG. 4. Proton NMR analysis of PCL-PEG-AT degradation in aqueous buffer of pH 5.0. As the acetal bond is being cleaved, peak a diminishes substantially, whereas peak b of the PCL segment is not expected to change much. Shown are day-3 samples at different pH. After day 3, the peak a continues to become smaller, because of the dissolution and loss of PEG chains.
Figure 5:
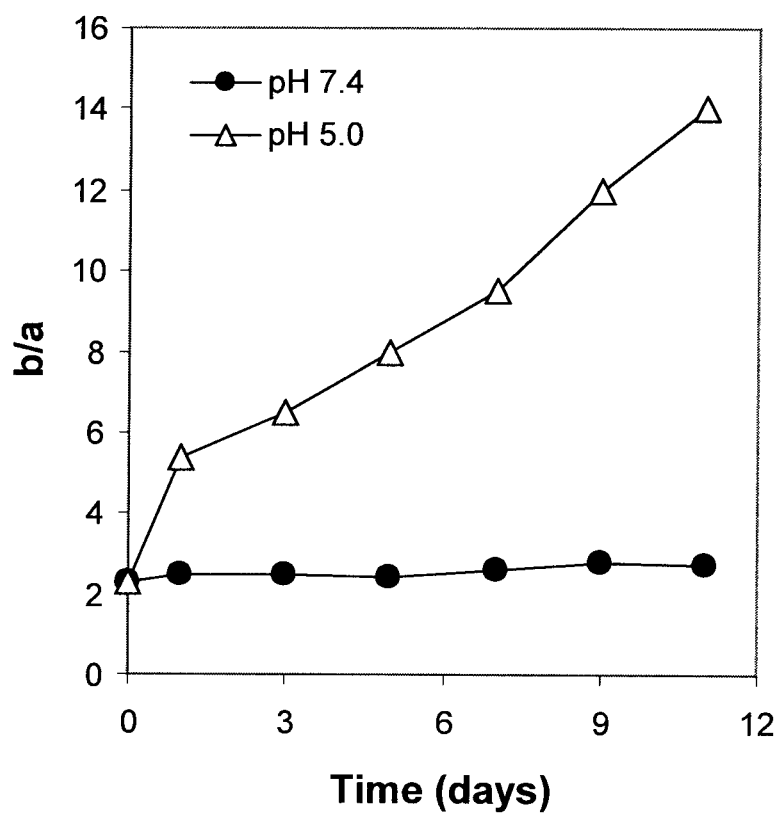
FIG. 5. Proton NMR analysis of PCL-PEG-AT hydrolysis: the ratio of peak area b/a, representing the degree of acetal hydrolysis of the polymer, increased substantially with time at pH 5.0 but changed little over time at pH 7.4. This observation is consistent with the measurement of mass loss at different pHs.
Figure 6:
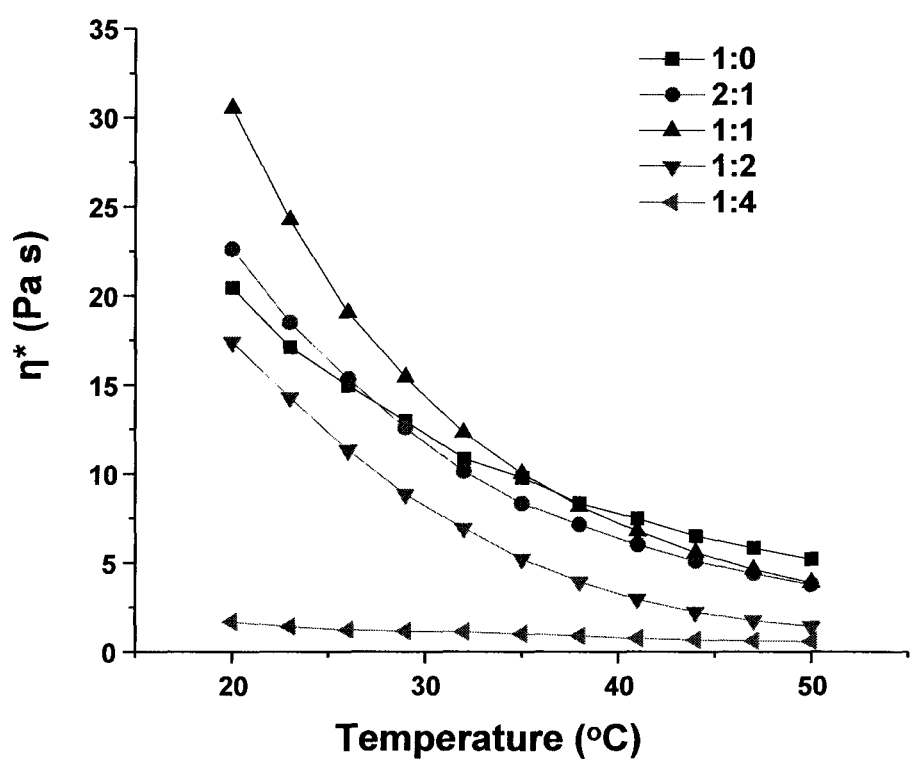
FIG. 6. Compound viscosity and temperature dependence of viscosity are dependent on the content of water in the polymer/water mixture. Shear frequency was 1 Hz. Notably, adding one part water to one part polymer increased the viscosity of the sample compared to polymer alone at room temperature. Mixing in more water further decreased viscosity of the mixture.
Figure 7:
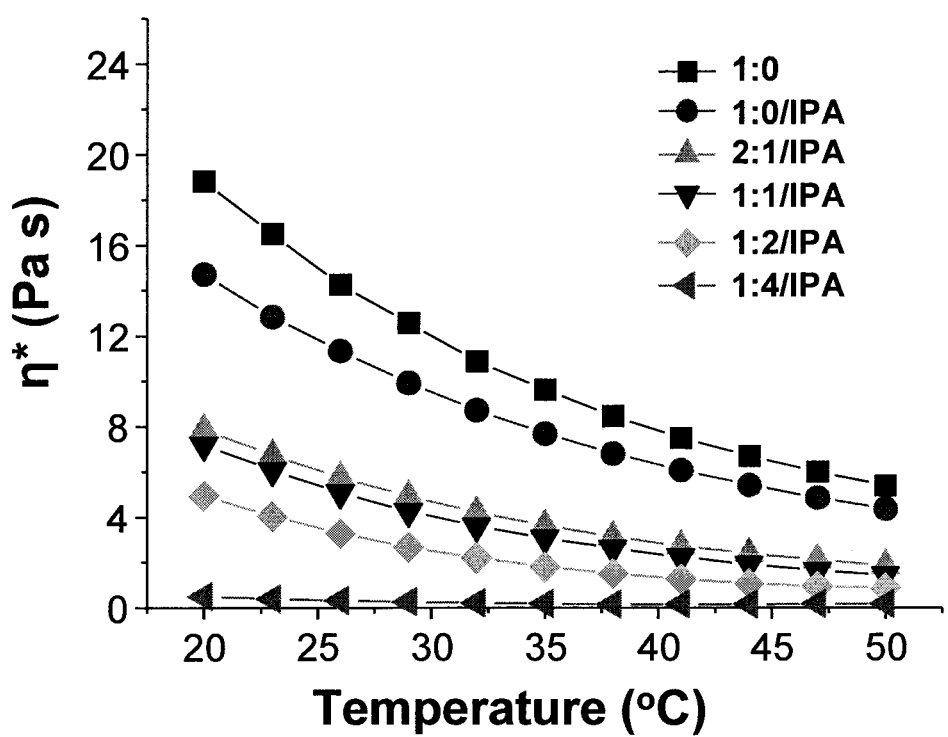
FIG. 7. Adding 5% isopropanol to the polymer or polymer/water mixtures significantly reduced the viscosity of the mixtures.
Figure 8:
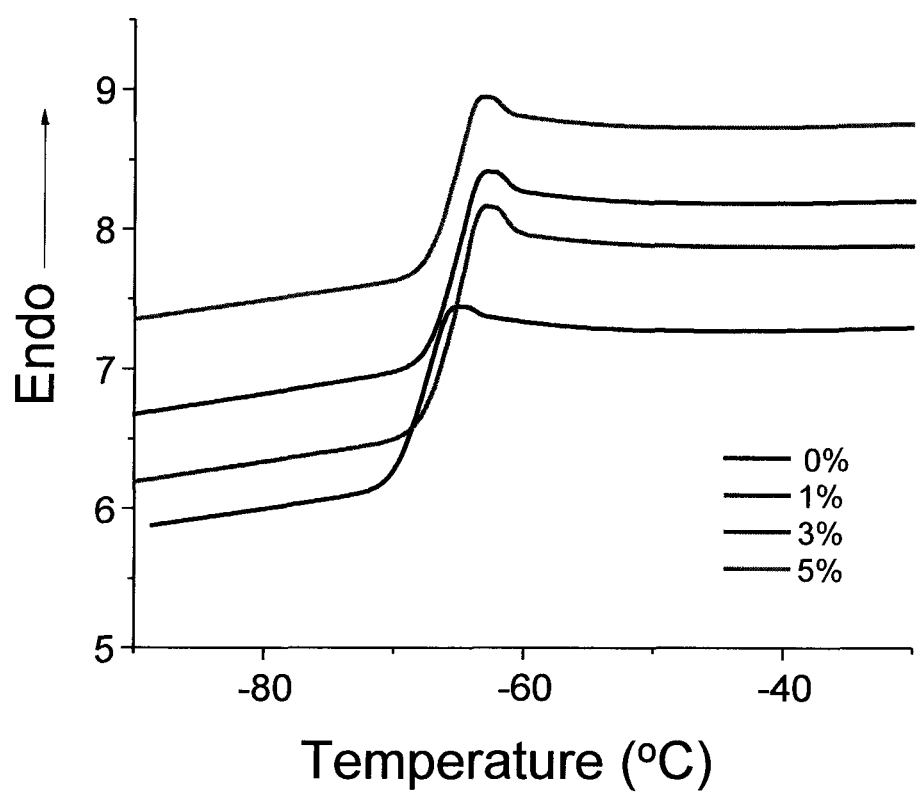
FIG. 8. DSC curves of PCL-PEG-AT semi-solid polymer alone and containing various loading of BSA. It can be seen that there was a very minor increase in glass transition temperature (Tg) in BSA-loaded polymer compared with polymer without BSA.
Figure 9:
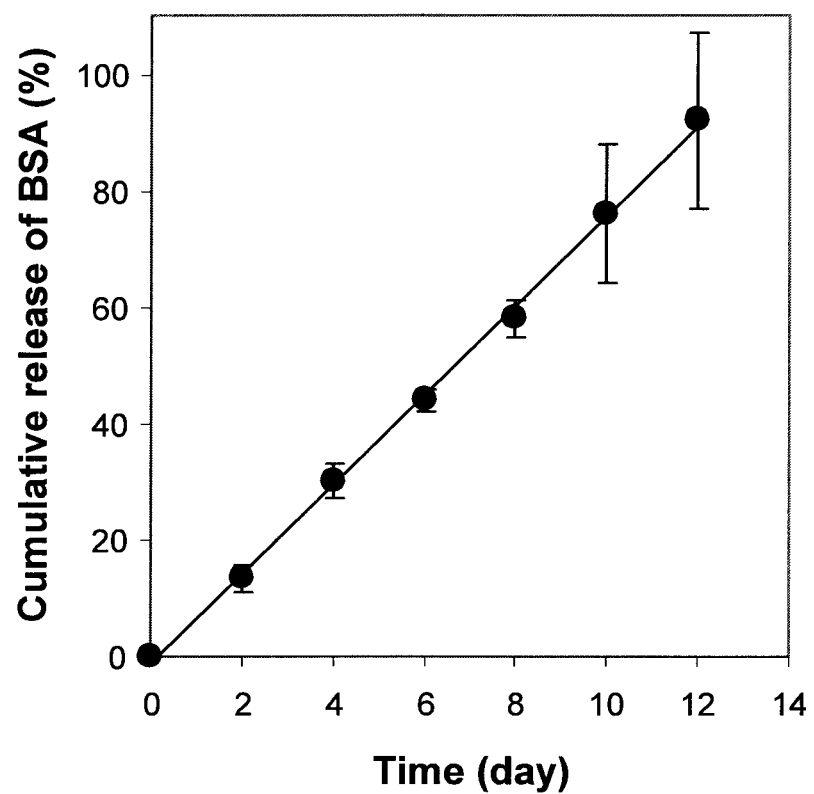
FIG. 9. Release kinetics of BSA from semi-solid PCL-PEG-AT. BSA: 3% loading, 37° C. Zero order and complete release by the end of 12 days have been achieved. The release rate and profile of BSA can be adjusted by altering the chemical composition of the polymer, or simple, by creating different mixtures of polymer/water containing dissolved protein.
Figure 10:
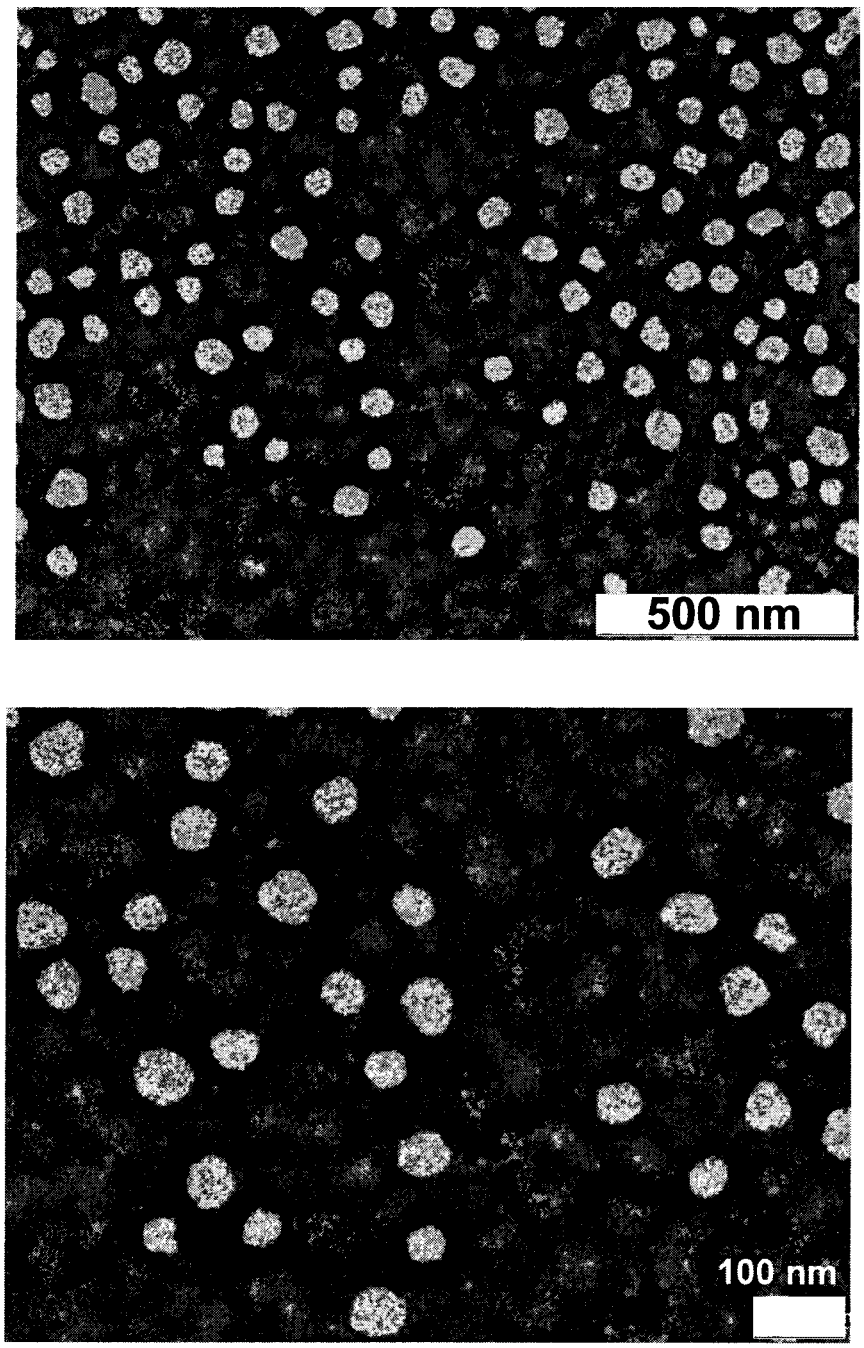
FIG. 10. The PCL-PEG-AT polymer was dispersed in PBS buffer (pH 7.4) at 0.2 mg/mL and the morphology of the nanoparticles is shown by TEM (below). The average particle size of the suspensions was measured using dynamic light scattering to be under 100 nm, which remained stable in pH 7.4 for at least 48 h. Therefore, the dispersion of the semi-solid polymer into large excess of aqueous buffer forming nanoparticles is a distinct feature of the PCL-PEG-AC polymers, which are amphiphilic in nature.
Figure 11:
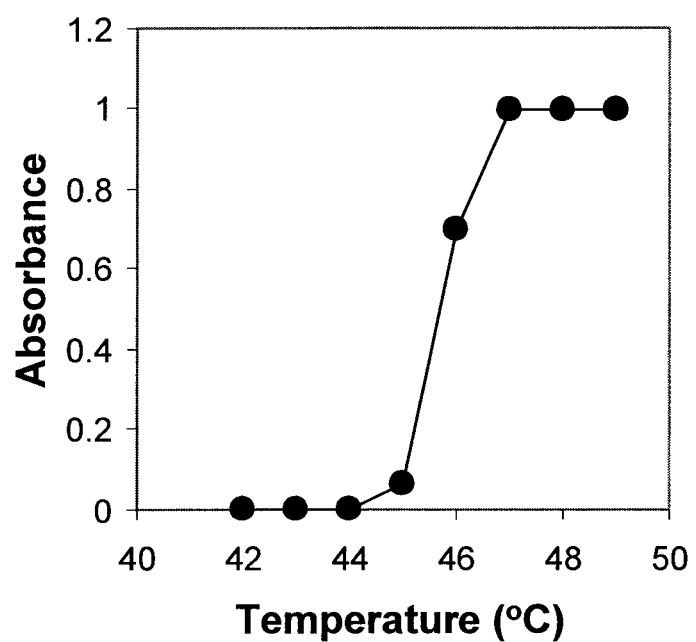
FIG. 11. PCL-PEG-PA nanoparticles in water undergo temperature responsive phase transition. At temperature below ~45° C., the 0.2 mg/mL solution of the nanoparticles was optically clear, however, it turned cloudy as temperature raised beyond 45° C. The temperature responsive phase transition behavior was also reversible. The temperature sensitive transition property is tunable by adjusting the composition of the polymer, such as using different divinyl ether monomer or using different ratios of PCL and PEG in the feed. This behavior suggests the possibility of using the nanoparticles as hyperthermia-controlled drug delivery vehicles.

The following definitions are used, unless otherwise described: halo is fluoro, chloro, bromo, or iodo. Alkyl denotes both straight and branched groups; but reference to an individual radical such as propyl embraces only the straight chain radical, a branched chain isomer such as isopropyl being specifically referred to. Aryl denotes a phenyl radical or a bicycle having about nine to ten ring atoms in which at least one ring is aromatic.

The abbreviation PCL means polycaprolactone. PEG means polyethylene glycol or alternatively referred to herein as polyethylene oxide (PEO) or polyoxyethylene (POE).

Specific values listed below for radicals, substituents, and ranges, are for illustration only; they do not exclude other defined values or other values within defined ranges for the radicals and substituents.

Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; and $(C_3-C_8)$cycloalkyl can be cyclopropyl, cyclobutyl, cyclopentyl, cyclohexyl, cycloheptyl, or cyclooctyl.

The polymers of the invention can be formulated as pharmaceutical compositions and administered to a mammalian host, such as a human patient in a variety of forms adapted to the chosen route of administration, e.g., oral, bucal, nasal, topical or injection. Pharmaceutical composition of the invention may also be implanted in a device, for example, under the skin for continuous slow release.

The polymers can be administered by injection in pure liquid form, or as solutions, or as dispersions. Solutions of the polymers can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions can be prepared by incorporating the polymers in the required amount, either in pure liquid form, or in the appropriate solvent with other ingredients enumerated above, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form. However, they may also be administered to the skin as compositions or formulations, in combination with a dermatologically acceptable carrier.

Useful dosages of the biologically active agents can be determined by comparing their in vitro activity, and in vivo activity in animal models. Methods for the extrapolation of effective dosages in mice, and other animals, to humans are known to the art; for example, see U.S. Pat. No. 4,938,949.

The amount of the biologically active agent required for use in treatment will vary not only with the particular biologically active agent selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Processes and intermediates for preparing polymers of formula I are provided as further embodiments of the invention. Polymers of the invention can be prepared using techniques that are similar to those described herein or they can be prepared using techniques that are known. For example, polymers of the invention can be prepared using procedures similar to those that are described in FIG. 1. The divinyl ether compound in THF with a trace amount of p-toluene sulfonic acid is reacted with PCL diol and PEG at room temperature overnight to a semi-solid polymer. Unreacted monomers and catalyst can be removed by dialysis against THF and then dried under vacuum.

Accordingly, in an aspect of the invention there is provided a polymer comprising 1) one or more polycaprolactone (PCL) units and 2) at least one or more polyethylene glycol (PEG) units; wherein at least one of said polycaprolactone units is conjugated to a PEG forming an acetal group.

In an embodiment, the polymer of the invention has a structure comprising one or more units according to formula I

(I)

wherein:

A is an acid-labile hydrolytically cleavable acetal group; and

PCL/PEG is either polycaprolactone or polyethylene glycol chain, or is a chain containing polylactone and polyethylene glycol groups.

In an embodiment, the polymer of formula I contains at least one PCL unit. In another embodiment, PCL/PEG is either a polycaprolactone chain or polyethylene glycol chain. In another embodiment, PCL/PEG Accordingly, in an embodiment of the invention there is provided a polymer comprising one or more units of formula II:

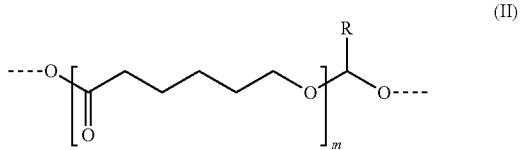
(II)

wherein:

R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl; and m in each occurrence is an integer from 1 to 50.

In an embodiment, a repeating unit of the polymer of the invention has a structure according to formula (III):

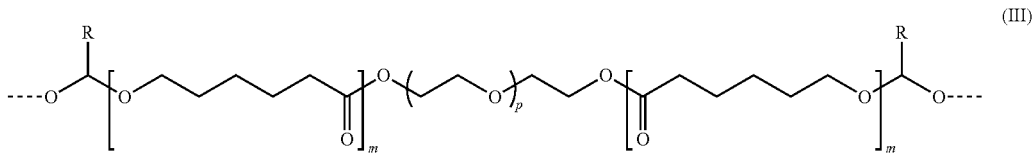
(III)

wherein

R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl;

m in each occurrence is an integer from 1 to 50; and p is an integer from 1 to 50.

In another embodiment, a repeating unit of the polymer of the invention has the structure according to formula (IV)

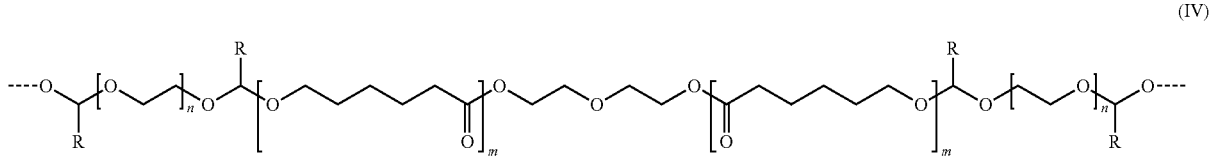
(IV)

wherein:

R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl;

m is an integer from 1 to 50; and n is an integer from 1 to 50.

In another embodiment, a repeating unit of the polymer of the invention has the structure according to formula (V)

$$\text{(V)}$$

wherein

R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl;

m is an integer from 1 to 50;

n is an integer from 1 to 50; and o is an integer from 1 to 50.

In one embodiment, the polymers of the invention do not comprise one or more units of polyethyleneoxide.

In one embodiment, the invention provides polymers that comprise one or more units of formula I.

In one embodiment, the invention provides polymers that comprise one or more units of formula II.

In one embodiment, the invention provides polymers that comprise one or more units of formula III.

In one embodiment, the invention provides polymers that comprise one or more units of formula IV.

In one embodiment, the invention provides polymers that comprise one or more units of formula V.

In one embodiment the invention provides polymers that comprise repeating units of formula I, II, III, IV or V.

In one embodiment the invention provides polymers that comprise repeating units of In one embodiment each R is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, or $(C_1-C_{10})$alkyl-O—$(C_1-C_{10})$alkyl;

In one embodiment R is $(C_1-C_{10})$alkyl.

In one embodiment R is methyl, ethyl, propyl, butyl, pentyl, or hexyl.

In one embodiment R is methyl, ethyl, propyl, butyl, pentyl, or hexyl.

In one embodiment R is $(C_1-C_6)$alkyl$(C_3-C_8)$cycloalkyl$(C_1-C_6)$alkyl.

In one embodiment R is methyl.

In one embodiment, m in each occurrence is independently 1 to 50. In one embodiment, m in each occurrence is independently 1 to 20. In one embodiment, m in each occurrence is independently 1 to 10. In one embodiment, m in each occurrence is independently 1 to 9. In one embodiment, m in each occurrence is independently 1 to 8. In one embodiment, m in each occurrence is independently 1 to 7. In one embodiment, m in each occurrence is independently 1 to 6. In one embodiment, m in each occurrence is independently 1 to 5. In one embodiment, m in each occurrence is independently 1 to 4. In one embodiment, m in each occurrence is independently 1 to 3. In one embodiment, m in each occurrence is independently 1 to 2. In one embodiment, m in each occurrence is 10. In one embodiment, m in each occurrence is 9. In one embodiment, m in each occurrence is 8. In one embodiment, m in each occurrence is 7. In one embodiment, m in each occurrence is 7. In one embodiment, m in each occurrence is 6. In one embodiment, m in each occurrence is. In one embodiment, m in each occurrence is 4. In one embodiment, m in each occurrence is 3. In one embodiment, m in each occurrence is 2. In one embodiment, m in each occurrence is 1.

In one embodiment, n in each occurrence is independently 1 to 50. In one embodiment, n in each occurrence is independently 1 to 20. In one embodiment, n in each occurrence is independently 1 to 10. In one embodiment, n in each occurrence is independently 1 to 9. In one embodiment, n in each occurrence is independently 1 to 8. In one embodiment, n in each occurrence is independently 1 to 7. In one embodiment, n in each occurrence is independently 1 to 6. In one embodiment, n in each occurrence is independently 1 to 5. In one embodiment, n in each occurrence is independently 1 to 4. In one embodiment, n in each occurrence is independently 1 to 3. In one embodiment, n in each occurrence is independently 1 to 2. In one embodiment, n in each occurrence is 10. In one embodiment, n in each occurrence is 9. In one embodiment, n in each occurrence is 8. In one embodiment, n in each occurrence is 7. In one embodiment, n in each occurrence is 7. In one embodiment, n in each occurrence is 6. In one embodiment, n in each occurrence is. In one embodiment, n in each occurrence is 4. In one embodiment, n in each occurrence is 3. In one embodiment, n in each occurrence is 2. In one embodiment, n in each occurrence is 1.

In one embodiment, o in each occurrence is independently 1 to 50. In one embodiment, o in each occurrence is independently 1 to 20. In one embodiment, o in each occurrence is independently 1 to 10. In one embodiment, o in each occurrence is independently 1 to 9. In one embodiment, o in each occurrence is independently 1 to 8. In one embodiment, o in each occurrence is independently 1 to 7. In one embodiment, o in each occurrence is independently 1 to 6. In one embodiment, o in each occurrence is independently 1 to 5. In one embodiment, o in each occurrence is independently 1 to 4. In one embodiment, o in each occurrence is independently 1 to 3. In one embodiment, o in each occurrence is independently 1 to 2. In one embodiment, o in each occurrence is 10. In one embodiment, o in each occurrence is 9. In one embodiment, o in each occurrence is 8. In one embodiment, o in each occurrence is 7. In one embodiment, o in each occurrence is 7. In one embodiment, o in each occurrence is 6. In one embodiment, o in each occurrence is. In one embodiment, o in each occurrence is 4. In one embodiment, o in each occurrence is 3. In one embodiment, o in each occurrence is 2. In one embodiment, o in each occurrence is 1.

In one embodiment, p in each occurrence is independently 1 to 50. In one embodiment, o in each occurrence is independently 1 to 20. In one embodiment, p in each occurrence is independently 1 to 10. In one embodiment, p in each occurrence is independently 1 to 9. In one embodiment, p in each occurrence is independently 1 to 8. In one embodiment, p in each occurrence is independently 1 to 7. In one embodiment, p in each occurrence is independently 1 to 6. In one embodiment, p in each occurrence is independently 1 to 5. In one embodiment, p in each occurrence is independently 1 to 4. In one embodiment, p in each occurrence is independently 1 to 3. In one embodiment, p in each occurrence is independently 1 to 2. In one embodiment, p in each occurrence is 10. In one embodiment, p in each occurrence is 9. In one embodiment, p in each occurrence is 8. In one embodiment, p in each occurrence is 7. In one embodiment, p in each occurrence is 7. In one embodiment, p in each occurrence is 6. In one embodiment, p in each occurrence is. In one embodiment, p in each occurrence is 4. In one embodiment, p in each occurrence is 3. In one embodiment, p in each occurrence is 2. In one embodiment, p in each occurrence is 1.

In one embodiment the polymer of the invention has a molecular weight of at least about 2000.

In one embodiment the polymer of the invention has a molecular weight of at least about 5000.

In one embodiment the polymer of the invention has a molecular weight of at least about 10,000.

In one embodiment the polymer of the invention has a molecular weight of less than about 50,000.

In one embodiment the polymer of the invention has a molecular weight of less than about 30,000.

In one embodiment the polymer of the invention has a molecular weight of less than about 20,000.

In one embodiment the polymer of the invention has a molecular weight of 15,000±10,000.

In one embodiment the polymer of the invention has a molecular weight of 15,000±5,000.

In one embodiment the polymer of the invention has a molecular weight of 20,000±5,000.

Polymers of the invention are useful as carriers for a variety of biologically active agents. The release of the biologically active agents from the polymers of the invention can be modified by blending the semi-solid polymer with buffer salts that control the pH environment. Another way is to control the molecular weight of the PCL segment. Yet another method is to change the structure of R Polycaprolactone Units PCL can be synthesized via ring opening polymerization of caprolactone using well-known methods. See: Labet M, Thielemans W, Synthesis of polycaprolactone: a review. Chem Soc Rev. 2009, 38(12), 3484-3504. Many PCL diols are commercially available.

The invention provides polymers that have one or more acetal groups linking PCL and/or PEG units to one another of formulae I-V.

In one embodiment of the invention the unit that comprises polycaprolactone is a homopolymer of caprolactone.

In one embodiment of the invention the unit that comprises polycaprolactone has the formula:

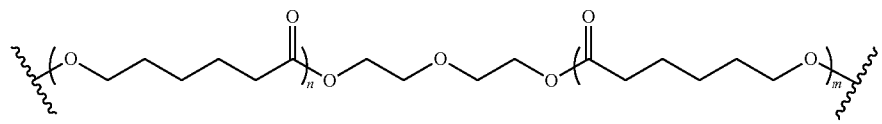

wherein n is an integer from 1-10 and m is an integer from 1-10.

In one embodiment of the invention the unit that comprises polycaprolactone is a copolymer of caprolactone and one or more other polymers that can be synthesized from ring opening polymerization.

In one embodiment of the invention a unit that comprises polycaprolactone can have the formula:

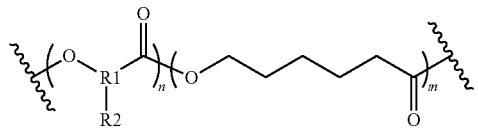

wherein: $R^1$ is $(C_1$-$C_{10})$alkyl, or $(C_1$-$C_{10})$alkenyl containing 1 to 3 double bonds; $R^2$ is hydrogen, $(C_1$-$C_{10})$alkyl, or $(C_1$-$C_{10})$alkenyl containing 1 to 3 double bonds, wherein the position at which $R^2$ is connected to $R^1$ can be at the α, β, γ, δ, ε, ζ carbon of $R^1$; m is an integer from 1-20; and n is an integer from 1-20.

In one embodiment of the invention at least 0.1 mol % of the polymer comprises polycaprolactone.

In one embodiment of the invention at least 1 mol % of the polymer comprises polycaprolactone.

In one embodiment of the invention at least 10 mol % of the polymer comprises polycaprolactone.

In one embodiment of the invention at least 25 mol % of the polymer comprises polycaprolactone.

In one embodiment of the invention at least 50 mol % of the polymer comprises polycaprolactone.

In one embodiment of the invention at least 75 mol % of the polymer comprises polycaprolactone.

In one embodiment of the invention at least 90 mol % of the polymer comprises polycaprolactone.

In one embodiment of the invention at least 95 mol % of the polymer comprises polycaprolactone.

In one embodiment of the invention the molecular weight of polycaprolactone in the polymer is at least 50.

In one embodiment of the invention the molecular weight of polycaprolactone in the polymer is at least 100.

In one embodiment of the invention the molecular weight of polycaprolactone in the polymer is at least 150.

In one embodiment of the invention the molecular weight of polycaprolactone in the polymer is at least 500.

In one embodiment of the invention the molecular weight of polycaprolactone in the polymer is at least 1000.

In one embodiment of the invention the molecular weight of polycaprolactone in the polymer is 3000±2000.

In one embodiment of the invention the molecular weight of polycaprolactone in the polymer is less than 5000.

In one embodiment of the invention the molecular weight of polycaprolactone in the polymer is less than 3000.

In one embodiment of the invention the molecular weight of polycaprolactone in the polymer is less than 2000.

In one embodiment of the invention the molecular weight of polycaprolactone in the polymer is less than 1000.

In one embodiment of the invention at least 0.1 mol % is polycaprolactone.

In one embodiment of the invention at least 1 mol % is polycaprolactone.

In one embodiment of the invention at least 10 mol % is polycaprolactone.

In one embodiment of the invention at least 25 mol % is polycaprolactone.

In one embodiment of the invention at least 50 mol % is polycaprolactone.

In one embodiment of the invention at least 75 mol % of the polymer is polycaprolactone.

In one embodiment of the invention at least 90 mol % of the polymer is polycaprolactone.

In one embodiment of the invention at least 95 mol % of the polymer is polycaprolactone.

In one embodiment of the invention at least 99 mol % of the polymer is polycaprolactone.

In one embodiment of the invention the molecular weight of the polymer is at least 50.

In one embodiment of the invention the molecular weight of the polymer is at least 100.

In one embodiment of the invention the molecular weight of the polymer is at least 150.

In one embodiment of the invention the molecular weight of the polymer is at least 500.

In one embodiment of the invention the molecular weight of the polymer is at least 1000.

In one embodiment of the invention the molecular weight of the polymer is 3000±2000.

In one embodiment of the invention the molecular weight of the polymer is less than 5000.

In one embodiment of the invention the molecular weight of the polymer is less than 3000.

In one embodiment of the invention the molecular weight of the polymer is less than 2000.

In one embodiment of the invention the molecular weight of the polymer is less than 1000.

Polyethyleneoxide (PEO or PEG) Units

The synthesis of PEG is well established in the literature, for example, see: J. Zhang, Y. Zhao, Z. Su, G. Ma, Synthesis of monomethoxy poly(ethylene glycol) without diol poly (ethylene glycol), J. Appl. Polym. Sci. 2007, 105(6), 3782-3786. Many PEG diols of various molecular weight are commercially available.

The invention provides polymers that have one or more acetal groups linking PEG and/or PCL units.

Biologically Active Agents

Polymers of the invention can be used to deliver a variety of biologically active agents. Examples of such agents include therapeutic agents (including small molecule drugs) and macromolecules (such as proteins, peptides, polysaccharides, and nucleic acids). For example, the polymers of the invention can be used to deliver agents that are useful for cancer therapy (anticancer drugs), anti-inflammatory therapy, anti-infectious therapy (such as antibiotics), neurological drug therapy including anesthetics for pain relief, antiangiogenic drugs, polysaccharides, vaccines, antigens, antibodies, cytokines, DNA and other polynucleotides, antisense oligonucleotides, RNA including small interfering RNA, and the like, and therapies to treat skin disorders and metabolic diseases such as diabetes. The polymers of the invention can also be used to deliver locally active agents such as astringents, antiperspirants, irritants, rubefacients, vesicants, sclerosing agents, caustics, escharotics, keratolytic agents, sunscreens and a variety of dermatologics including hypopigmenting and antipruritic agents. Other agents that can be delivered by this polymer includes biocides such as fungicides, pesticides, and herbicides, plant growth promoters or inhibitors, preservatives, disinfectants, air purifiers and nutrients. See for example U.S. Pat. No. 6,613,355.

Antigens that could be used at a dose of 1-1,000,000 µg or protein or cell number: antigens could include tumor cells (irradiated, frozen, lysed, dried), tumor-associated peptides, tumor neoantigens that result from genetic mutation in the somatic tumor cells, aberrantly glycolsylated tumor proteins, tumor cell membranes, or DNA encoding any of the above.

Adjuvants that could be used at a dose of 1-1,000,000 µg: toll-like receptor agonists such as but not limited to CpG, PolyIC, Imiquimod (or any imidazoquinoline-derivative of Imiquimod), Resiquimod, Flagellin.

The invention will now be illustrated by the following non-limiting Examples.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

Example 1

Materials

Polycaprolactone (PCL) diol (average $M_n$=530), polyethylene glycol (PEG) diol (average $M_n$=400), tri(ethylene glycol) divinyl ether, 1,4-butanediol divinyl ether, para-toluenesulfonic acid monohydrate (pTSA), tetrahydrofuran (THF), acetone, ammonium hydroxide, isopropanol, and bovine serum albumin (BSA) were purchased from Sigma. PCL diol and PEG diol were dried in a vacuum oven overnight. THF was dried over sodium. Other chemicals were used as received.

Polymerization

Dried PCL diol (2.65 g) and PEG diol (2 g) were added to a reaction flask through syringe under nitrogen atmosphere. Dried THF (10 mL) was added to dissolve PCL diol and PEG diol completely under stirring. Tri(ethylene glycol) divinyl ether (2.02 g) was then added to the flask and stirred for 5 min. Under stirring 0.5 weight % of pTSA in THF was added as catalyst. The polymerization continued under stirring for 6 h at room temperature, and a few drop of ammonium hydroxide was added to stop the reaction. THF was then removed by rotary evaporation to obtain the crude product as viscous liquid. To purify the crude product, it was dissolved in THF and dialyzed against THF of twice the volume using a membrane with a molecular weight cut-off of 3500. The dialysis continued for 2 days, during which the dialysate was changed every 4 h. The semi-solid polymer product was obtained after removing THF by rotary evaporation and drying under vacuum for 2 days at room temperature.

Characterization $^1$H NMR spectra of polymers were recorded on a Varian Unity spectrometer (300 MHz) with $CDCl_3$ as solvent. Molecular weight and distribution of polymers was measured by gel permeation chromatography on a GPC system (Wyatt Technology Corporation with DAWN DSP laser photometer) in THF at a flow rate of 1 mL/min and 25° C. Differential Scanning Calorimetry (DSC) was carried out over a temperature range of 100° C. to 150° C. using a TA Q100 calorimeter purged with nitrogen. The heating/cooling rate was 10° C./min. The midpoint of the transition zone was taken as the glass transition temperature ($T_g$).

Polymer Erosion In Vitro and Analyses of Degradation Products

Semi-solid polymer samples (80 mg, $W_0$) were placed in 8 mL of buffer of different pH (50 mM phosphate: pH 7.4 or 50 mM acetate, pH 5.0) and incubated at 37° C. At certain time points the polymer was removed, dried and weighed ($W_1$). Polymer mass loss ($W_{loss}$) was calculated from 100× ($W_0$−$W_1$)/$W_0$. Triplicate samples were measured for each time point and the average values were reported. The samples were analyzed by GPC in $CHCl_3$ and by proton NMR in $CDCl_3$.

Rheology of Semi-Solid Polymer and Water Mixtures

The semi-solid polymers were mixed with various amounts of water at room temperature. The polymer/water weight ratio was varied from 2:1 to 1:4. A small amount of isopropanol (IPA) was also added to 5% by weight to either the semi-solid polymer alone or the various polymer/water mixtures. In all cases, all the samples were homogeneous and optically transparent with no sign of phase separation, aggregation or precipitation. The rheological behavior of the samples was measured with an AR-G2 rheometer (TA Instrument, Ltd) equipped with parallel plates (25 mm in diameter). The gap between parallel plates was adjusted to around 1 mm. The dynamic strain sweep measurement was first performed to ensure that the materials were in their linear viscoelastic range. The complex viscosity ($\eta^*$) was recorded as a function of temperature (from 20 to 80° C., 3° C. per step) at a constant shear frequency of 1 Hz.

Protein Loading and Release Kinetics

To load the semi-solid polymer with drugs, BSA was dissolved in PBS and mixed with polymer to produce 1%, 3%, and 5% loading by weight and then lyophilized. DSC curves of the polymer with the above BSA loading were obtained. To determine release kinetics, 50 mg of drug loaded polymer was placed in small nylon bags (200-mesh) and immersed in 6 mL of buffered saline (20 mM phosphate, pH 7.4 or 20 mM acetate, pH 5.0) at 37° C. At various time points, supernatant was removed for analysis of drug content and replaced with the same amount of fresh buffer. The BSA concentration in the supernatant was measured by the absorbance at 595 nm with a Quick Start™ Bradford Protein Assay kit.

Dispersion of Polymer into Excess Water to Form Temperature-Sensitive Nanoparticles The semi-solid polymer was dispersed in excess PBS at pH 7.4 (0.2 mg/mL) and applied to a carbon grid. After staining with uranyl acetate, the morphology of the nanoparticles was examined by transmission electron microscopy (TEM). The average particle size was also determined by dynamic light scattering. The nanoparticle dispersion was heated at 1° C. per min until the dispersion turned from transparent to opaque and the absorbance (turbidity) was measured at 500 nm.

Solubilization of Nile Red in Water Aided by the Semi-Solid Polymer.

Nile Red (NR) is a hydrophobic molecule that is insoluble in water. 3 mg of NR solid particles suspended in 1 mL of aqueous phosphate buffered saline (PBS) without dissolving. With addition of 10% semi-solid polymer (100 mg), NR is completely solubilized in PBS to 3 mg/mL. This observation suggests that nanoparticles formed by semi-solid polymer in water can be used to greatly enhance the solubility of poorly water-soluble drug molecules, which will be expected to have higher bioavailability and therapeutic efficacy in patients.

Cellular Uptake of Nile Red-Loaded Nanoparticles by Human Glioma Cells

Figure 12:
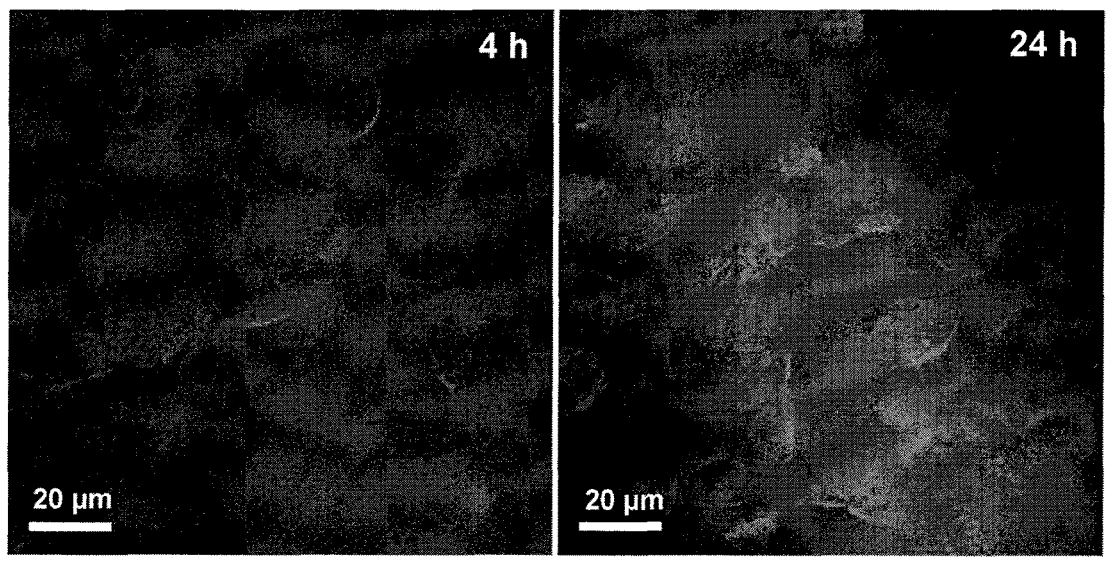
FIG. 12. Uptake of Nile Red (NR)-loaded nanoparticles by human glioma T98G cells at 4 h and 24 h.
Figure 13:
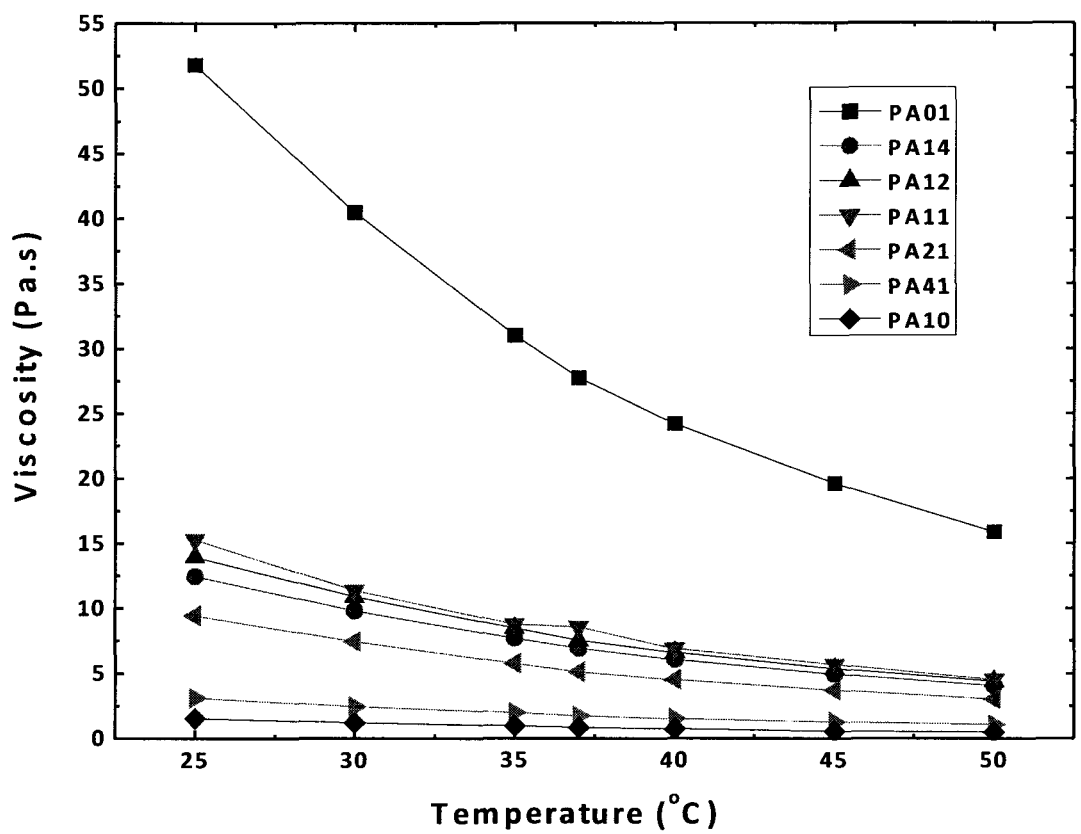
FIG. 13. Temperature dependent changes in viscosity of the PA series of the semi-solid polymers.

Human glioma T98G cells were plated on two 4-well chamber slides (Lab-Tek) at a density of 60,000 cells per well in low-glucose DMEM media containing 10% FBS (both from Gibco) and were cultured for 24 h. After washing the cells with PBS, fresh media with 10% FBS was added. In separate chamber slides, NR-loaded semi-solid polymer nanoparticles were added to the cells and allowed to incubate at 37° C., 5% CO2, and 99% humidity for 4 and 24 h. Prior to imaging, cell media was removed and cells were washed twice with cold PBS and fixed using BD Cytofix (BD Biosciences) at 4° C. for 10 min. The cells were then mounted using VectaShield (Vector Laboratories) mounting media containing DAPI to label the cell nucleus. Images of cellular uptake of NR-loaded nanoparticles were captured with an Olympus FV1000 IX2 inverted confocal microscope using a 40×/1.30NA Olympus oil objective and FV10-ASW imaging software (Olympus). NR was excited at 485 nm and emission was detected at 525 nm. A nitrogen laser with a wavelength of 405 nm was used to excite DAPI and emission was detected using a 405-505 nm band-pass filter. Captured images were then merged in Image-J software with the median z-slice image used for representation. See FIG. 12.

Preparation of Polymer with Varying Molar Ratio of PEG and PCL

By varying the molar ratio of PEG and PCL in the feed, a series of semi-solid polymers with various hydrophobicity/hydrophilicity was synthesized with very high yield. The total molar quantity of PEG and PCL was equivalent to the molar quantity of the divinyl ether (linker) to ensure that the polycondensation reaction progressed optimal. If the molar ratio of the diols and divinyl ether deviated from 1, the molecular weight of the polymer products would be reduced.

| Polymer | $M_{PEG}/M_{PCL}$ | $M_{diol}:M_{ester}$ | $M_{PEG}$ (mmol) | $M_{PCL}$ (mmol) | $M_{linker}$ (mmol) | Yield (%) |
|---|---|---|---|---|---|---|
| PA01 | 0:1 | 1:1 | 0 | 30 | 30 | 98.2 |
| PA14 | 1:4 | 1:1 | 6 | 24 | 30 | 98.7 |
| PA12 | 1:2 | 1:1 | 10 | 20 | 30 | 95.8 |
| PA11 | 1:1 | 1:1 | 15 | 15 | 30 | 96.6 |
| PA21 | 2:1 | 1:1 | 20 | 10 | 30 | 95.8 |
| PA41 | 4:1 | 1:1 | 24 | 6 | 30 | 97.7 |
| PA10 | 1:0 | 1:1 | 30 | 0 | 30 | 97.2 |

Physico-Chemical Properties of the Polymers

Number average molecular weight (Mn) and weight average molecular weight (Mw) and polydispersity index (PDI) was measured by gel permeation chromatography (GPC).

Density (ρ) of the polymers ranges from 1.1 to 1.2. Glass transition temperature ($T_g$) of the polymers ranges from −63 to −67° C. Viscosity (η), however, varies greatly depending on the polymer composition. The most hydrophobic polymer (PA01) was the most viscous and the most hydrophilic polymer (PA10) was the least.

| Polymer | Mn | Mw | PDI | ρ (g/mL) | Tg (° C.) | $\eta_{25° C.(Pa\,S)}$ |
|---|---|---|---|---|---|---|
| PA01 | 19400 | 28500 | 1.46 | 1.13 | −63.08° C. | 51.8 |
| PA14 | 12900 | 19800 | 1.53 | 1.19 | −63.06° C. | 12.4 |
| PA12 | 14000 | 20700 | 1.47 | 1.13 | −66.16° C. | 14.0 |
| PA11 | 10900 | 16300 | 1.49 | 1.16 | −66.37° C. | 15.3 |
| PA21 | 13400 | 18900 | 1.41 | 1.16 | −64.29° C. | 9.4 |
| PA41 | 8300 | 13200 | 1.60 | 1.19 | −63.57° C. | 3.1 |
| PA10 | 9500 | 15200 | 1.60 | 1.18 | −63.51° C. | 1.5 |

What is claimed is:

1. A polymer comprising 1) one or more polycaprolactone (PCL) units and 2) at least one or more polyethylene glycol (PEG) units; wherein at least one of said polycaprolactone units is conjugated to a PEG unit forming an acetal group, wherein said polymer comprises one or more units of formula (I):

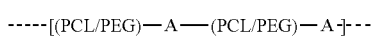

-----[(PCL/PEG)—A——(PCL/PEG)—A-]---     (I)

wherein:

A is an acid-labile, hydrolytically cleavable acetal group; and PCL/PEG is either a polycaprolactone or a polyethylene glycol chain, or is a chain containing polycaprolactone and polyethylene glycol groups.

2. The polymer of claim 1, wherein each PCL is a homopolymer of caprolactone.

3. The polymer of claim 1 which comprises one or more units of formula II:

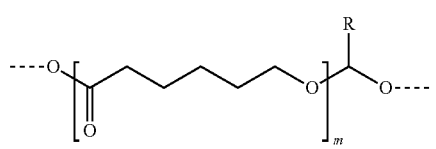

(II)

wherein:

R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl; and m in each occurrence is an integer from 1 to 50.

4. The polymer of claim 3 wherein R is $(C_2-C_{10})$alkyl.

5. The polymer of claim 1 which comprises one or more units of formula (III):

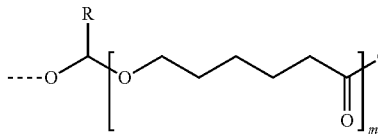 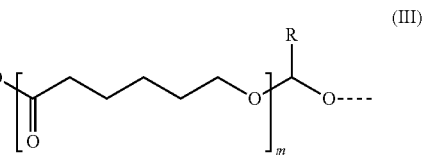

(III)

wherein

R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl;

m in each occurrence is an integer from 1 to 50; and
p is an integer from 1 to 50.

6. The polymer of claim 1 which comprises one or more units of formula (IV)

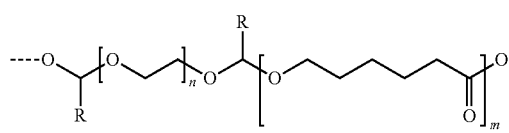 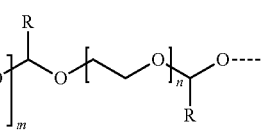

(IV)

wherein:

R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl; and m in each occurrence is an integer from 1 to 50;

n in each occurrence is an integer from 1 to 50.

7. The polymer of claim 1 which comprises one or more units of formula (V)

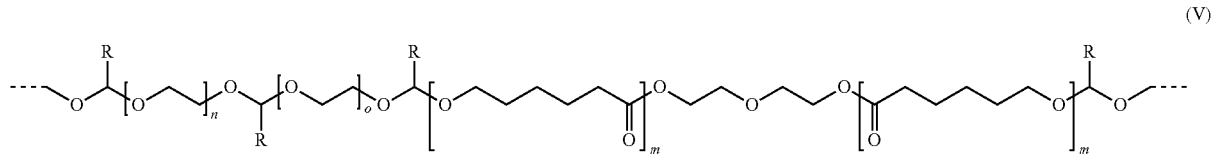

wherein
R in each occurrence is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl;

m in each occurrence is an integer from 1 to 50;
n is an integer from 1 to 50; and
o is an integer from 1 to 50.

8. The polymer of claim 1 which has a molecular weight of at least about 2000.

9. The polymer of claim 1 which has a molecular weight of at least about 10,000.

10. The polymer of claim 1 which has a molecular weight of less than about 50,000.

11. The polymer of claim 1 which has a molecular weight of 15,000±10,000.

12. The polymer of claim 1 comprising one or more units of the formula:

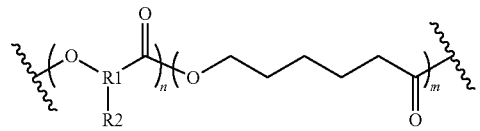

wherein: $R^1$ is $(C_1-C_{10})$alkyl, or $(C_1-C_{10})$alkenyl containing 1 to 3 double bonds; $R^2$ is hydrogen, $(C_1-C_{10})$alkyl, or $(C_1-C_{10})$alkenyl containing 1 to 3 double bonds, wherein the position at which $R^2$ is connected to $R^1$ can be at the α, β, γ, δ, ε, ζ carbon of $R^1$; m is an integer from 1-20; and n is an integer from 1-20.

13. The polymer of claim 1 comprising polyethyleneoxide having a molecular weight of no more than about 2000.

14. The polymer of claim 1 comprising polyethyleneoxide having a molecular weight of no more than about 1000.

15. A pharmaceutical composition comprising a polymer as described in claim 1 and a biologically active agent.

16. The composition of claim 15 wherein the biologically active agent is selected from small molecular drugs, large molecular drugs, proteins, antibodies, peptides, polysaccharides, nucleic acids.

17. The composition of claim 16 wherein the biologically active agent is a tumor antigen or immunostimulatory adjuvant.

18. The composition of claim 15 wherein the biologically active agent is a tumor cell, a tumor-associated peptide, a tumor neoantigen from genetic mutation in somatic tumor cells, an aberrantly glycolsylated tumor protein, tumor cell membrane, or DNA encoding any of the above.

19. The composition of claim 15, wherein the biologically active agent is CpG oligodeoxynucleotide, polyinosinic-polycytidylic acid (polyIC), imiquimod, an imidazoquinoline-derivative of imiquimod, resiquimod, or flagellin.

* * * * *